United States Patent [19]

Chabardes et al.

[11] Patent Number: 4,463,196
[45] Date of Patent: Jul. 31, 1984

[54] PROCESS FOR THE PREPARATION OF CITRAL

[75] Inventors: Pierre Chabardes, Saint-Foy-les-Lyon; Emile Kuntz, Lyons, both of France

[73] Assignee: Rhone-Poulenc Industries, Paris, France

[21] Appl. No.: 147,740

[22] Filed: May 8, 1980

Related U.S. Application Data

[63] Continuation of Ser. No. 752,270, Dec. 14, 1976, abandoned.

[30] Foreign Application Priority Data

Dec. 19, 1975 [FR] France ............................... 75 39784

[51] Int. Cl.³ ............................................ C07C 45/67
[52] U.S. Cl. .................................................. 568/450
[58] Field of Search .......................................... 568/450

[56] References Cited

U.S. PATENT DOCUMENTS

| | | | |
|---|---|---|---|
| 2,524,865 | 10/1950 | Winslow | 568/450 |
| 2,524,866 | 10/1950 | Winslow | 568/450 |
| 2,853,520 | 9/1958 | Newman | 568/450 |
| 3,912,250 | 11/1975 | Pauling | 568/450 |
| 3,920,751 | 11/1975 | Chabardes | 568/450 |
| 3,994,936 | 11/1976 | Andrews et al. | 568/450 |

FOREIGN PATENT DOCUMENTS 96548  10/1972  France ............................... 568/450

*Primary Examiner*—Werren B. Lone
*Attorney, Agent, or Firm*—Burns, Doane, Swecker & Mathis

[57] ABSTRACT

Citral is prepared by heating dehydrolinalol in the presence of a vanadium compound as catalyst and an alkanol of 12 to 18 carbon atoms as co-catalyst, whereby isomerization is effected. There may also be present an alkanol or cycloalkanol of 7 to 11 carbon atoms as co-catalyst.

9 Claims, No Drawings

PROCESS FOR THE PREPARATION OF CITRAL

This is a continuation of application Ser. No. 752,270, filed Dec. 14, 1976, now abandoned.

BACKGROUND OF THE INVENTION

1. Field of the Invention

The present invention relates to the isomerization of dehydrolinalol (3,7-dimethyl-oct-6-en-3-olyne) of formula

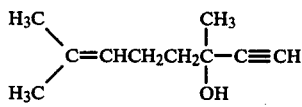

to citral (3,7-dimethyl-octa-2,6-dienal) of formula

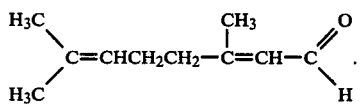

2. Description of the Prior Art

U.S. Pat. No. 3,920,751 describes the isomerization of acetylenic alcohols to ethylenic carbonyl compounds in the presence of catalysts based on metals selected from the group consisting of V, Mo, W, Nb and Re. This same patent also discloses the possibility of using small amounts of co-catalysts, in particular alcohols, cyclohexanol being the compound most commonly used.

U.S. Pat. No. 3,912,250 also deals with a similar isomerization in the presence of silanyl vanadates combined with large quantities of solvents (paraffins, nitrobenzene, silicone oil and mesitylene).

Further, U.S. Pat. No. 3,912,656 discloses the same isomerization by means of silanyl vanadate combined with rather large quantities of silanol.

SUMMARY OF THE INVENTION

It is a primary object of the present invention to provide a process for the isomerization of dehydrolinalol to citral which is improved in its performance.

Another object of the invention is to provide an industrially economical process for the isomerization of dehydrolinalol.

Another object of the invention is to provide a process for the isomerization of dehydrolinalol which gives citral in improved yield.

Another object of the invention is to provide a process for the isomerization of dehydrolinalol which makes it possible to avoid the use of large amounts of solvents, which can greatly decrease the productivity of an apparatus of a given size, the productivity being the amount of reaction product obtained per unit time and per unit volume of the reactor.

Another object of the invention is to provide an isomerization process which avoids the use of relatively expensive co-catalysts, such as the silanols.

It has now been found that these objects can readily be achieved by a process which forms the subject of the present invention. This process for the preparation of citral from dehydrolinalol comprises, in its broader aspect, heating dehydrolinalol in the presence of a catalyst based on a vanadium compound and in the presence of an alkanol of 12 to 18 carbon atoms in which the alkyl moiety may be straight or branched chain, the numerical ratio $$\frac{\text{number of mols of co-catalyst}}{\text{number of gram atoms of vanadium}}$$

being between 3 and 500 and preferably between 6 and 150.

According to a narrower preferred aspect of the invention, a second co-catalyst is also present, which consists of an alkanol or cycloalkanol (optionally an alkylcycloalkanol) of from 7 to 11 carbon atoms. This second co-catalyst is present in such amounts that the numerical ratio $$\frac{\text{number of mols of the combined co-catalysts}}{\text{number of gram atoms of vanadium}}$$

is within the limits indicated for the amount of the first co-catalyst.

DETAILED DESCRIPTION OF THE INVENTION

The catalysts based on a vanadium compound which can be used in accordance with the present invention are vanadium compounds, such as those mentioned in U.S. Pat. No. 3,920,751, the disclosure of which is incorporated herein by reference. The preferred catalysts are oxygen-containing compounds containing a group having one of the following formulae:

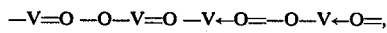

wherein the atom V can be joined to other atoms by ionic or covalent bonds. As the catalyst, particularly advantageous compounds are the vanadates, which may be salts or esters derived from alcohols or from silanols. The esters are often more advantageous for use than the salts. Furthermore, since dehydrolinalol and citral are known to have a tendency to instability, both in a basic and in an acid medium, it is obvious that it is advantageous to work under conditions which avoid the reaction mixture assuming an acid or basic character.

As suitable catalysts, there may be mentioned alkyl vanadates, such as methyl vanadate, ethyl vanadate, propyl vanadate, hexyl vanadate, decyl vanadate, lauryl vanadate, octadecyl vanadate, tetrahydrolinalyl vanadate; other aliphatic vanadates such as dehydrolinalyl vanadate, triethanolamine vanadate; cycloaliphatic vanadates, such as cyclohexyl vanadate; aryl vanadates, such as phenyl vandate; and silyl vanadates, such as triphenylsilyl vanadate.

The amount of catalyst is such that the weight of vanadium (in the combined state) is between 0.0001% and 5% of the weight of the dehydrolinalol and preferably between 0.01 and 2%.

As with the known processes, the process according to the invention can be carried out in the presence or absence of a solvent. If a solvent is used, it should be substantially inert so as not to react chemically with the catalyst or the reactants. In particular, they can be chlorinated or non-chlorinated aliphatic, cycloaliphatic or aromatic hydrocarbons, nitrated aromatic hydrocarbons, ethers or amides.

As the first co-catalyst suitable for use in the practice of the process according to the invention, there may be mentioned lauryl alcohol, myristyl alcohol, palmityl alcohol and stearyl alcohol, also referred to as n-dodecan-1-ol, n-tetradecan-1-ol, n-hexadecan-1-ol and n-octadecan-ol, respectively, and alkanepolyols (preferably diols).

As the second co-catalyst which may be used, there may be mentioned n-octan-1-ol, n-heptan-1-ol, n-decan-1-ol, 2-ethyl-cyclohexanol and 2-ethyl-hexan-1-ol.

The reaction temperature is generally between 50° and 300° C. and preferably between 120° and 220° C.

When the reaction is complete, the reaction product is isolated by any conventional means, generally by distillation. In the practice of the invention, it is preferred to distill the unreacted dehydrolinalol, the citral and, when present, the second more volatile co-catalyst, leaving the catalyst and the first less volatile co-catalyst as a residue which can be directly re-used for fresh isomerizations. According to a preferred technique, a flash distillation is first carried out, which gives a distillate containing the unreacted dehydrolinalol, the citral and, when used, the volatile co-catalyst, and then, in a second stage, this mixture is subjected to a fractional distillation to separate the dehydrolinalol from the citral and, when present, from the second co-catalyst.

In addition to the advantages already mentioned, the process of the invention makes it possible to obtain good yields of citral and a high degree of conversion of the dehydrolinalol (DHL).

The examples which follow are set forth to illustrate the invention. The alkanols mentioned in these examples are primary alkanols with a non-branched carbon chain but this is not to be considered as limiting the invention.

EXAMPLE 1

0.56 g of cyclohexyl orthovanadate, 20.16 g of octadecanol and 50 g of dehydrolinalol are introduced into a 125 cm$^3$ three-neck flask equipped with a nitrogen inlet and a distillation column. The mixture is rapidly heated to 160° C., with stirring and is then maintained at this temperature for 25 minutes, after which it is cooled to 60° C. and distilled under a reduced pressure of 0.3 mm Hg, while heating the reactor to 130° C. The process is repeated twice, each time introducing 50 g of DHL into the distillation residue and then heating at 160° C. for 25 minutes, and then seven more times, each time introducing 50 g of DHL into the residue of the preceding distillation and heating at 165° C. for 25 minutes. The amount of dehydrolinalol and citral present in the distillate is determined in each instance.

The following table in which DC denotes the degree of conversion of the dehydrolinalol and Y denotes the yield of citral relative to the dehydrolinalol converted shows the results obtained in each operation:

TABLE 1

| Operation No. | Temperature | DC | Y |
|---|---|---|---|
| 1 | 160° C. | 14% | 96% |
| 2 | 160° C. | 15% | 98% |
| 3 | 160° C. | 16% | 91% |
| 4 | 165° C. | 24% | 99% |
| 5 | 165° C. | 21% | 97% |
| 6 | 165° C. | 24% | 96% |
| 7 | 165° C. | 26% | 96% |
| 8 | 165° C. | 23% | 91% |
| 9 | 165° C. | 24% | 100% |
| 10 | 165° C. | 23% | 96% |

EXAMPLE 2

1.28 go of octadecyl orthovanadate, 19.13 g of octadecanol and 50 g of dehydrolinalol are introduced into a 125 cm$^3$ three-neck flask equipped with a nitrogen inlet and a distillation column. The mixture is rapidly heated to 165° C., with stirring and is then maintained at this temperature for 25 minutes, after which it is cooled to 60° C. and distilled under a reduced pressure of 0.3 mm Hg, while heating the reactor to 130° C. The dehydrolinalol and the citral are determined in the distillates.

The process is repeated several times, under varying conditions of reaction temperature and time. The results obtained in accordance with this example are reported in the following table:

TABLE II

| Operation No. | Reaction temperature | Duration of the reaction | DC | Y |
|---|---|---|---|---|
| 1 | 165° C. | 25 mins. | 19% | 94% |
| 2 | 165° C. | 40 mins. | 29% | 96% |
| 3 | 165° C. | 25 mins. | 19% | 96% |
| 4 | 175° C. | 25 mins. | 37% | 93% |
| 5 | 175° C. | 30 mins. | 46% | 90% |
| 6 | 165° C. | 1 hr. | 33% | 96% |

EXAMPLE 3

0.53 g of cyclohexyl orthovanadate, 6.72 g of octadecanol, 50 g of dehydrolinalol, and 10 cm$^3$ of paraffin oil of high boiling point are introduced into a 125 cm$^3$ three-neck flask equipped with a nitrogen inlet and a distillation column. The mixture is rapidly heated to 150° C., with stirring and is then maintained at this temperature for 25 minutes, after which it is cooled to 60° C. and distilled under a reduced pressure of 0.3 mm Hg, while heating the reactor to 130° C. The process is repeated four times by introducing a further 50 g of DHL into the preceding distillation residue and then heating at 160° C. for 30 minutes. The dehydrolinalol and the citral are determined in each of the distillates.

The results of this example are set forth in the following table:

TABLE III

| Operation No. | Temperature | DC | Y |
|---|---|---|---|
| 1 | 150° C. | 10% | 89% |
| 2 | 160° C. | 21% | 95% |
| 3 | 160° C. | 23% | 91% |
| 4 | 160° C. | 21% | 91% |
| 5 | 160° C. | 25% | 90% |

EXAMPLE 4

Operating as described in Example 3 but using 0.53 g of cyclohexyl orthovanadate and 10.6 of tetradecanol, results are obtained as set forth in the following table:

TABLE IV

| Operation No. | Reaction temperature | Duration of the reaction | DC | Y |
|---|---|---|---|---|
| 1 | 160° C. | 25 mins. | 19% | 92% |
| 2 | 160° C. | 25 mins. | 22% | 94% |
| 3 | 160° C. | 25 mins. | 22% | 95% |
| 4 | 160° C. | 25 mins. | 22% | 95% |
| 5 | 160° C. | 33 mins. | 28% | 94% |

EXAMPLE 5

1.28 g of octadecyl orthovanadate and 20.16 g of octadecanol are introduced into a 100 cm$^3$ flask which is equipped with a dropping funnel, an argon inlet, a distillation column and a stirrer, with provision for connection with a vacuum pump, and the mixture is then heated at 180° C. while reducing the pressure to 150 mm Hg. A first quantity of 20.32 g of dehydrolinalol is run in over 1 hour 15 minutes and, at the same time, the volatile products are distilled. The reactor is then heated to 200° C. under a reduced pressure of 100 mm Hg, after which a second quantity of 20.46 g of dehydrolinalol is run in over 1 hour and 20 minutes and, at the same time, the volatile products are distilled. Thereafter the reactor is cooled and volatile products are then removed at 140° C. under a reduced pressure of 0.1 mm Hg. Analyses carried out on the distillate showed that the degree of conversion of the dehydrolinalol (DC) is 30% and the yield (Y) of citral is 82%. 5.01 g of DHL are introduced into the distillation residue and the whole is heated to 200° C. for 25 minutes and then cooled. The volatile product is removed by distillation carried out at 100° C. to 140° C. under a reduced pressure of 0.1 mm Hg. The degree of conversion (DC) of the dehydrolinalol is 94% and the yield of citral (Y) is 92%. The same operation is carried out a second time, introducing 5.12 g of dehydrolinalol, and the degree of conversion of the dehydrolinalol is found to be 95% and the yield of citral 82%. On introducing a further 5.08 g of dehydrolinalol and heating at 200° C. for 15 minutes, the degree of conversion of the dehydrolinalol is found to be 78%, and the yield of citral 93%.

EXAMPLE 6

0.56 g (1.54×10$^{-3}$ mols) of cyclohexyl orthovanadate, 4.65 g of dodecanol and 50.02 g of dehydrolinalol are introduced into a 125 ml three-neck flask equipped with a nitrogen inlet and a distillation column. The mixture is rapidly heated to 160° C., with stirring, and is kept at this temperature for 25 minutes. It is then cooled to 30° C. and the volatile products are distilled under a pressure reduced to 0.5 mm Hg. The distillate (49.56 g) is analyzed and found to contain 41.0 g of dehydrolinalol and 8.2 g of citral. The degree of conversion of the dehydrolinalol is 18% and the yield of citral relative to the dehydrolinalol which has disappeared is 91%.

EXAMPLE 7

1.27 g (1.45×10$^{-3}$ mols) of octadecyl orthovanadate, 1.18 g (4.35×10$^{-3}$ mols) of octadecanol, 7.34 g (5.7×10$^3$) mols) of octanol and about 50 g of dehydrolinalol are introduced into a 125 cm$^{-3}$ three-neck flask equipped with a nitrogen inlet and a distillation column. The mixture is rapidly heated to 160° C. and is kept at this temperature for 25 minutes. It is then cooled to 60° C. and the volatile products are distilled under a pressure reduced to 0.3 mm Hg; the distillation residue is heated to 130° C. and then cooled. About 7.4 g of octanol and about 50 g of dehydrolinalol are again introduced and the operation is repeated four times.

The dehydrolinalol and the citral are determined in the distillates, and the following table shows the results obtained:

TABLE V

| Operation No. | DHL introduced | Octanol introduced | DC | Y |
|---|---|---|---|---|
| 1 | 49.91 g | 7.34 g | 14% | 93% |
| 2 | 50.10 g | 7.43 g | 15% | 93% |
| 3 | 50.11 g | 7.30 g | 15% | 95% |
| 4 | 50.18 g | 7.28 g | 17% | 93% |

We claim:
1. In a process for the preparation of citral, comprising heating dehydrolinalol at a temperature within the range of 50° to 300° C., in the presence of a vanadium compound containing a group having one of he following formulae:

a catalyst, to isomerize the dehydrolinalol to citral, and recovering the citral from the reaction medium, the improvement which comprises the inclusion of an alkanol having 12 to 18 carbon atoms as co-catalyst in the reaction medium.
2. A process as claimed in claim 1 in which there is also present as a second co-catalyst an alkanol or cycloalkanol of from 7–11 carbon atoms.
3. A process as claimed in claim 1, in which said vanadium compound is a vanadate in the form of an ester.
4. A process as claimed in claim 1 in which the ratio $$\frac{\text{number of mols of co-catalyst}}{\text{number of gram atoms of vanadium}}$$

is between 3 and 500.
5. A process as claimed in claim 4 in which the ratio is between 6 and 150.
6. A process as claimed in claim 2 in which the ratio $$\frac{\text{number of mols of combined co-catalysts}}{\text{number of gram atoms of vanadium}}$$

is between 6 and 150.
7. A process as claimed in claim 1 in which said range is 120° C. to 220° C.
8. A process as claimed in claim 1 in which upon completion of isomerization, the citral and any unreacted dehydrolinalol are distilled off leaving said catalyst and co-catalyst in the distillation residue, introducing additional dehydrolinalol into said residue and repeating said process.
9. A proces as claimed in claim 2 in which upon completion of isomerization, the citral, any unreacted dehydrolinalol and said second co-catalyst are distilled off leaving said catalyst and first co-catalyst in the distillation residue, introducing additional dehydrolinalol and said second co-catalyst into said residue and repeating said process.

* * * * *